United States Patent [19]

Fey et al.

[11] Patent Number: 5,407,948
[45] Date of Patent: Apr. 18, 1995

[54] SUBSTITUTED MONO- AND BIPYRIDYLMETHYLPYRIDONES

[75] Inventors: Peter Fey; Walter Hübsch, both of Wuppertal; Jürgen Dressel, Radevormwald; Rudolf Hanko, Essen; Thomas Krämer; Ulrich Müller, both of Wuppertal; Matthias Müller-Gliemann, Solingen; Martin Beuck, Erkrath; Hilmar Bischoff, Wuppertal; Stefan Wohlfeil, Hilden; Dirk Denzer; Stanislav Kazda, both of Wuppertal; Johannes-Peter Stasch, Solingen; Andreas Knorr, Erkrath; Siegfried Zaiss, Wuppertal, all of Germany

[73] Assignee: Bayer Aktiengesellschaft, Leverkusen, Germany

[21] Appl. No.: 239,197

[22] Filed: May 6, 1994

[30] Foreign Application Priority Data

May 13, 1993 [DE] Germany .................. 43 16 077.8

[51] Int. Cl.$^6$ .............. C07D 401/14; C07D 401/10; A61K 31/44; A61K 31/53
[52] U.S. Cl. .................. 514/333; 514/335; 546/256; 546/261
[58] Field of Search ........... 546/256, 261; 514/333, 514/335

[56] References Cited

U.S. PATENT DOCUMENTS

| 5,128,327 | 7/1992 | Chakravarty et al. | 514/81 |
| 5,149,699 | 9/1992 | Ellingboe et al. | 514/258 |

FOREIGN PATENT DOCUMENTS

| 0500297 | 8/1992 | European Pat. Off. | 514/335 |
| 0504888 | 9/1992 | European Pat. Off. | 514/333 |
| 0508393 | 10/1992 | European Pat. Off. | 514/333 |
| 0508445 | 10/1992 | European Pat. Off. | 514/333 |
| 0530702 | 3/1993 | European Pat. Off. | 514/335 |

OTHER PUBLICATIONS

The Journal of Cell Biology, vol. 50, 1971, pp. 172–186; "The Smooth Muscle Cell", R. Ross.

Primary Examiner—C. Warren Ivy
Assistant Examiner—Zinna N. Davis
Attorney, Agent, or Firm—Sprung Horn Kramer & Woods

[57] ABSTRACT

Substituted mono- and bipyridylmethylpyridones are prepared either by reaction of pyridones with mono- or bipyridylmethylhalogen compounds or by reaction of pyridone-substituted halogenopyridines with tetrazolylphenylboronic acids. The substituted mono- and bipyridylmethylpyridones can be employed as active compounds in medicaments, in particular for the treatment of arterial hypertension and atherosclerosis.

10 Claims, No Drawings

SUBSTITUTED MONO- AND BIPYRIDYLMETHYLPYRIDONES

The invention relates to substituted mono- and bipyridylmethylpyridones, processes for their preparation and their use in medicaments, in particular as antihypertensive and anti-atherosclerotic agents.

It is known that renin, a proteolytic enzyme, splits off the decapeptide angiotensin I from angiotensinogen in vivo, angiotensin I in turn being broken down to the hypertensive octapeptide angiotensin II in the lung, the kidneys or other tissues. The various effects of angiotensin II, such as, for example, vasoconstriction, $Na^+$ retention in the kidney, release of aldosterone in the adrenal gland and an increase in the tonicity of the sympathetic nervous system act synergistically in the sense of increasing blood pressure.

Angiotensin II moreover has the property of promoting the growth and multiplication of cells such as, for example, cardiac muscle cells and smooth muscle cells, these growing to an increased extent and proliferating with various disease states (for example hypertension, atherosclerosis and cardiac insufficiency).

In addition to inhibition of renin activity, a possible use for intervention in the renin-angiotensin system (RAS) is inhibition of the activity of angiotensin converting enzyme (ACE) and blockade of angiotensin II receptors.

Arylheteroarylalkyl-substituted triazoles and imidazoles are known as A II antagonists from the publications EP 508 445, EP 503 393, EP 504 888 and U.S. Pat. No. 5,128,327.

The invention relates to substituted mono- and bipyridylmethylpyridones of the general formula (I)

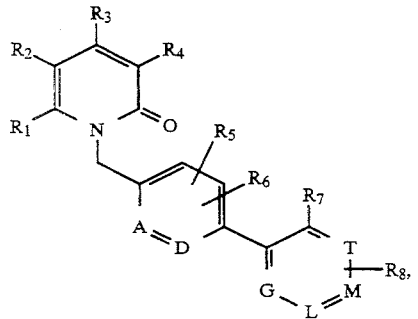

in which
A,D,G,L,M and T are identical or different and represent the CH group or represent a nitrogen atom, but wherein at least one of the radicals represents a nitrogen atom, but in each ring at most only one of the radicals represents a nitrogen atom, $R^1$ represents straight-chain or branched alkyl having up to 10 carbon atoms, which is optionally substituted by cycloalkyl having 3 to 6 carbon atoms, hydroxyl or by straight-chain or branched alkoxy or alkylthio having in each case up to 6 carbon atoms, or represents cycloalkyl having 3 to 6 carbon atoms, $R^2$, $R^3$ and $R^4$ are identical or different and represent hydrogen, hydroxyl, nitro, cyano, formyl or halogen, or represent straight-chain or branched alkyl, alkenyl, alkinyl, alkoxy or alkylthio having in each case up to 8 carbon atoms, which are optionally substituted up to 3 times in an identical or different manner by hydroxyl, cyano, halogen, carboxyl, straight-chain or branched alkoxy, acyl or alkoxycarbonyl having in each case up to 6 carbon atoms, or by cycloalkyl having 3 to 6 carbon atoms, benzyl, phenyl, phenoxy, benzoyl or by a 5- to 7-membered, saturated or unsaturated heterocyclic radical having up to 3 hetero atoms from the series comprising S, N and O, it being possible for the cyclic radicals in turn to be substituted up to 2 times in an identical or different manner by trifluoromethyl, trifluoromethoxy, halogen, nitro, cyano, hydroxyl, hydroxymethyl or by straight-chain or branched alkyl or alkoxy having in each case up to 6 carbon atoms, or represent straight-chain or branched acyl or alkoxycarbonyl having in each case up to 8 carbon atoms, phenoxycarbonyl, benzyloxycarbonyl or carboxyl, or represent tetrazolyl, which is optionally substituted by triphenylmethyl or by straight-chain or branched alkyl having up to 6 carbon atoms, which can in turn be substituted by cyano, halogen, carboxyl, phenoxycarbonyl, hydroxyl or by straight-chain or branched alkoxy or alkoxycarbonyl having in each case up to 6 carbon atoms, or represent a group of the formula

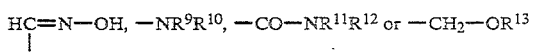

wherein
$R^9$, $R^{10}$, $R^{11}$ and $R^{12}$ are identical or different and denote hydrogen, cycloalkyl having 3 to 8 carbon atoms or straight-chain or branched alkyl having up to 8 carbon atoms, which is optionally substituted by phenyl, or $R^9$ and $R^{10}$, together with the nitrogen atom, form a 5- to 6-membered, saturated heterocyclic radical having up to 2 further hetero atoms from the series comprising S, N and O, $R^{13}$ denotes straight-chain or branched acyl having up to 6 carbon atoms or benzoyl, $R^5$, $R^6$ and $R^8$ are identical or different and represent hydrogen, halogen, cyano, nitro, hydroxyl, trifluoromethyl or amido or represent straight-chain or branched alkyl, alkoxy or alkoxycarbonyl having up to 6 carbon atoms, $R^7$ represents a group of the formula $-CO-R^{14}$, $-SO_2R^{15}$, $-CO-NR^{16}R^{17}$, $-NH-SO_2R^{18}$, or denotes $-SO_2NR^{19}R^{20}$, wherein $R^{14}$ denotes hydroxyl or straight-chain or branched alkoxy having up to 6 carbon atoms, $R^{15}$ denotes hydroxyl, trifluoromethyl, straight-chain or branched alkoxy or alkyl having in each case up to 6 carbon atoms, phenyl or benzyl, which can optionally be substituted up to 2 times in an identical or different manner by halogen, trifluoromethyl or straight-chain or branched alkyl having up to 4 carbon atoms, $R^{16}$ and $R^{17}$ are identical or different and have the abovementioned meaning of $R^{11}$ and $R^{12}$, or $R^{16}$ denotes hydrogen and $R^{17}$ denotes the group $-SO_2R^{15}$, wherein $R^{15}$ has the abovementioned meaning, $R^{18}$ has the abovementioned meaning of $R^{15}$ and is identical to or different from this, $R^{19}$ and $R^{20}$ have the abovementioned meaning of $R^9$ and $R^{10}$ and are identical to or different from these, or $R^{19}$ denotes hydrogen or straight-chain or branched alkyl having up to 4 carbon atoms and $R^{20}$ has the abovementioned meaning of $R^{15}$ and is identical to or different from this, or $R^7$ represents a radical of the formula

wherein $R^{21}$ denotes hydrogen or straight-chain or branched alkyl having up to 8 carbon atoms, which is optionally substituted by straight-chain or branched acyl having up to 6 carbon atoms, or denotes the triphenylmethyl group, and salts thereof.

The substituted mono- and bipyridylmethylpyridones according to the invention can also be in the form of their salts. Salts with organic or inorganic bases or acids may be mentioned in general here.

Physiologically acceptable salts are preferred in the context of the present invention. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal salts or ammonium salts of the compounds according to the invention which possess a free carboxyl group or a tetrazolyl radical. Particularly preferred salts are, for example, those of sodium, potassium, magnesium or calcium, and ammonium salts which are derived from ammonia or organic amines such as, for example, ethylamine, di- or triethylamine, di- or triethanolamine, dicyclohexyl amine, dimethylaminoethanol, arginine, lysine, ethylenediamine or 2-phenylethylamine.

The compounds according to the invention can exist in stereoisomeric forms which are either of one another mirror images (enantiomers) or are not (diastereomers). The invention relates both to the enantiomers or diastereomers or to particular mixtures thereof. The racemic forms, like the diastereomers, can be separated into the stereoisomerically uniform constituents in a known manner.

A heterocyclic radical in general represents a 5- to 7-membered, preferably 5- to 6-membered, saturated or unsaturated ring which can contain up to 2 oxygen, sulphur and/or nitrogen atoms as hetero atoms. 5- and 6-membered rings with one oxygen, sulphur and/or up to 2 nitrogen atoms are preferred. Rings which may be mentioned as preferred are: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl, piperazinyl or tetrazolyl.

A 5- to 6-membered, saturated heterocyclic radical which furthermore can contain up to 2 oxygen, sulphur and/or nitrogen atoms as hetero atoms in general represents azetidinyl, piperidyl, morpholinyl, piperazinyl or pyrrolidyl. Morpholinyl is preferred.

Preferred compounds of the general formula (I) are those in which

A,D,G,L,M and T are identical or different and represent the CH group or represent a nitrogen atom, but wherein at least one of the radicals represents a nitrogen atom, but in each ring at most only one of the radicals represents a nitrogen atom, $R^1$ represents straight-chain or branched alkyl having in each case up to 8 carbon atoms, which is optionally substituted by cyclopropyl, cyclopentyl, cyclohexyl, hydroxyl or by straight-chain or branched alkoxy or alkylthio having in each case up to 4 carbon atoms, or represents cyclopropyl, cyclopentyl or cyclohexyl, $R^2$, $R^3$ and $R^4$ are identical or different and represent hydrogen, hydroxyl, nitro, cyano, formyl, fluorine, chlorine, bromine or iodine, or represent straight-chain or branched alkyl, alkenyl, alkinyl, alkoxy or alkylthio having in each case up to 6 carbon atoms, which are optionally substituted by hydroxyl, cyano, fluorine, chlorine, bromine, carboxyl, straight-chain or branched alkoxy, acyl or alkoxycarbonyl having in each case up to 4 carbon atoms, or by benzyl, phenyl, phenoxy, benzoyl or thienyl, it being possible for the cyclic radicals in turn to be substituted by trifluoromethoxy, trifluoromethyl, hydroxymethyl, fluorine, chlorine, bromine, iodine or by straight-chain or branched alkyl or alkoxy having in each case up to 6 carbon atoms, or represent straight-chain or branched acyl or alkoxycarbonyl having in each case up to 6 carbon atoms, phenoxycarbonyl, benzyloxycarbonyl or carboxyl, or represent tetrazolyl, which is optionally substituted by triphenylmethyl or by straight-chain or branched alkyl having up to 5 carbon atoms, which can in turn be substituted by cyano, fluorine, chlorine, bromine, carboxyl, hydroxyl or by straight-chain or branched alkoxy or alkoxycarbonyl having in each case up to 4 carbon atoms, or represent a group of the formula

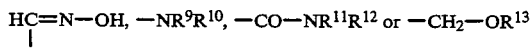

wherein $R^9$, $R^{10}$, $R^{11}$ and $R^{12}$ are identical or different and denote hydrogen, cyclopropyl, cyclopentyl, cyclohexyl or straight-chain or branched alkyl having up to 6 carbon atoms, which is optionally substituted by phenyl, or $R^9$ and $R^{10}$, together with the nitrogen atom, form a morpholine ring, $R^{13}$ denotes straight-chain or branched acyl having up to 6 carbon atoms or benzoyl, $R^5$, $R^6$ and $R^8$ are identical or different and represent hydrogen, fluorine, chlorine, bromine, trifluoromethyl or hydroxyl or represent straight-chain or branched alkyl or alkoxy having in each case up to 4 carbon atoms, $R^7$ represents a group of the formula —CO—$R^{14}$, —SO$_2$$R^{15}$, —CO—NR$^{16}$R$^{17}$, —NH—SO$_2$R$^{18}$ or —SO —NR$^{19}$R$^{20}$, wherein $R^{14}$ denotes hydroxyl or straight-chain or branched alkoxy having up to 4 carbon atoms, $R^{15}$ denotes straight-chain or branched alkyl having up to 4 carbon atoms, benzyl, trifluoromethyl or p-tolyl, $R^{16}$ and $R^{17}$ are identical or different and have the abovementioned meaning of $R^{11}$ and $R^{12}$ or denotes hydrogen and $R^{17}$ denotes the group —SO$_2$R$^{15}$, wherein $R^{15}$ has the abovementioned meaning, $R^{18}$ has the abovementioned meaning of $R^{15}$ and is identical to or different from this, $R^{19}$ and $R^{20}$ have the abovementioned meaning of $R^9$ and $R^{10}$ and are identical to or different from these, or $R^{19}$ denotes hydrogen or methyl, $R^{20}$ has the abovementioned meaning of $R^{15}$ and is identical to or different from this or $R^7$ represents a radical of the formula

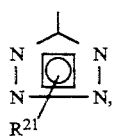

wherein $R^{21}$ denotes hydrogen or straight-chain or branched alkyl having up to 6 carbon atoms, which is optionally substituted by straight-chain or branched acyl having up to 4 carbon atoms, or denotes the triphenylmethyl group, and salts thereof.

Particularly preferred compounds of the general formula (I) are those in which

A,D,G,L,M and T are identical or different and represent the CH group or represent a nitrogen atom, but wherein at least one of the radicals represents a nitrogen atom, but in each ring at most only one of the radicals represents a nitrogen atom, $R^1$ represents straight-chain or branched alkyl having up to 6 carbon atoms, or represents cyclopropyl, cyclopentyl or cyclohexyl, $R^2$, $R^3$ and $R^4$ are identical or different and represent hydrogen, hydroxyl, cyano, formyl, fluorine, chlorine, bromine or iodine, or represent straight-chain or branched alkyl or alkoxy having in each case up to 4 carbon atoms, or represent straight-chain or branched alkoxycarbonyl having up to 4 carbon atoms, phenoxycarbonyl, benzyloxycarbonyl or carboxyl, or $R^5$, $R^6$ and $R^8$ are identical or different and represent hydrogen, hydroxyl, fluorine, chlorine, bromine or methyl, $R^7$ represents a group of the formula —CO—R$^{14}$, wherein $R^{14}$ denotes hydroxyl or straight-chain or branched alkoxy having up to 4 carbon atoms, or $R^7$ represents the tetrazolyl radical of the formula

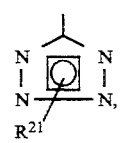

wherein $R^{21}$ denotes hydrogen or straight-chain or branched alkyl having up to 4 carbon atoms, which is optionally substituted by straight-chain or branched acyl having up to 4 carbon atoms, or denotes the triphenylmethyl group, and salts thereof.

Very particularly preferred compounds of the general formula (I) are those in which A or D represents a nitrogen atom and the other substituents represent the CH group, $R^1$ represents straight-chain or branched alkyl having up to 4 carbon atoms, $R^2$, $R^3$ and $R^4$ are identical or different and represent hydrogen, carboxyl or benzyloxycarbonyl or represent straight-chain or branched alkoxycarbonyl having up to 4 carbon atoms, $R^5$, $R^6$ and $R^8$ are identical or different and represent hydrogen, fluorine, chlorine, bromine or methyl, $R^7$ represents a group of the formula —CO—R$^{14}$, wherein $R^{14}$ denotes hydroxyl or straight-chain or branched alkoxy having up to 4 carbon atoms or $R^7$ represents the tetrazolyl radical of the formula

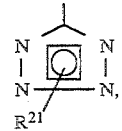

wherein $R^{21}$ denotes hydrogen or the triphenylmethyl group, and salts thereof.

Processes have furthermore been found for the preparation of the compounds of the general formula (I) according to the invention, characterized in that

[A] pyridones of the general formula (II)

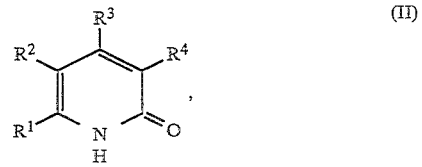

in which $R^1$, $R^2$, $R^3$ and $R^4$ have the abovementioned meaning, are reacted with compounds of the general formula (III)

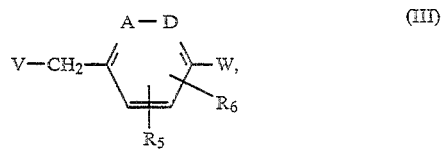

in which

A, D, $R^5$ and $R^6$ have the abovementioned meaning,

V represents halogen, preferably bromine, and

W represents a radical of the formula

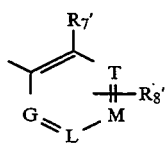

wherein

G, L, M, T and $R^8$ have the abovementioned meaning, $R^{7'}$ represents $C_1-C_4$-alkoxycarbonyl or, preferably, represents a radical of the formula

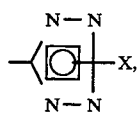

wherein

X denotes the triphenylmethyl group or hydrogen, in inert solvents in the presence of a base and if appropriate with addition of a catalyst, or

[B] compounds of the general formula (IV)

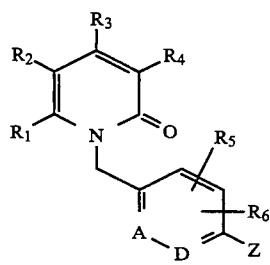

in which $R^1$, $R^2$, $R^3$, $R^4$, $R^5$, $R^6$, A and D have the abovementioned meaning and Z represents a typical leaving group, such as, for example, bromine, iodine or methane-, toluene-, fluoro- or trifluoromethanesulphonyloxy, preferably bromine, are reacted with compounds of the general formula (V) or (Va)

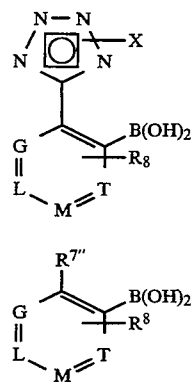

in which

G,L,M,T,$R^8$ and X have the abovementioned meaning and $R^{7''}$ has the abovementioned meaning of $R^7$ but does not represent the tetrazolyl radical, in inert solvents in the presence of a base and under metal catalysis, and, in the case where X=a triphenylmethyl group, this is subsequently eliminated with acids in organic solvents and/or water under customary conditions, and, if appropriate, in the case of the carbonyl radicals listed under the substituents $R^7$ and/or $R^{7'}$, derivatization is carried out by customary methods, after hydrolysis of the particular esters, for example by amidation or sulphoamidation, and, in the case of the salts, the products are reacted with acids or bases, preferably starting from the free tetrazole ($R^{22}$/X=H), and, in the case of the free acid ($R^7$=CO$_2$H) and the free tetrazole ($R^{21}$=H), the products are reacted with acids, starting from the salts, and, if appropriate, the other substituents are also varied by known methods.

The process according to the invention can be illustrated by way of example by the following equation:

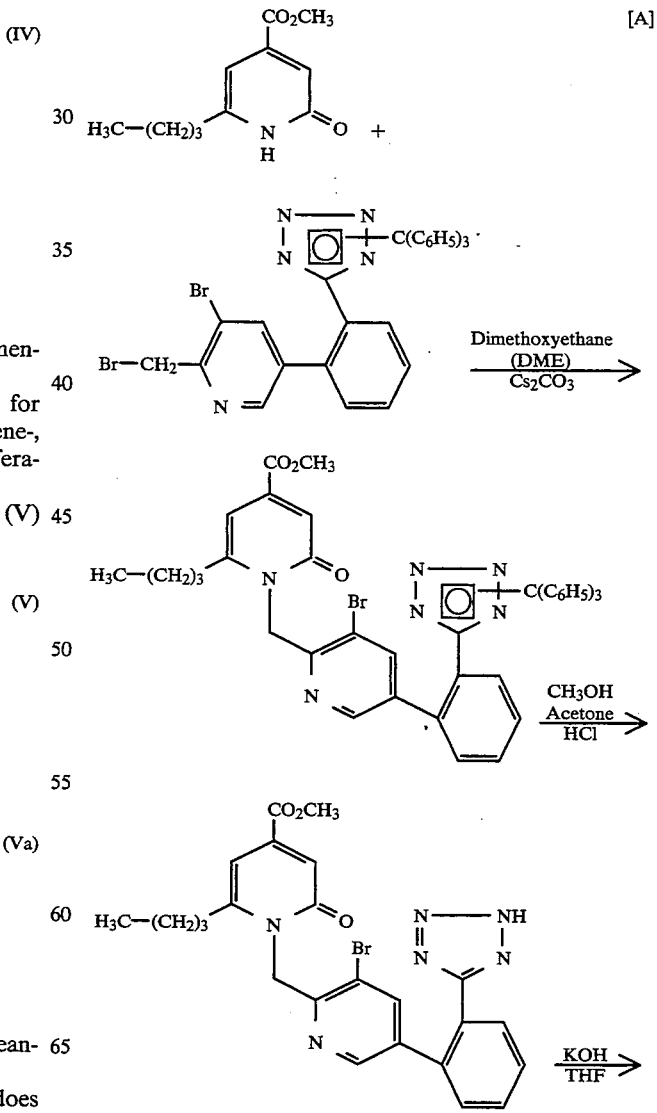

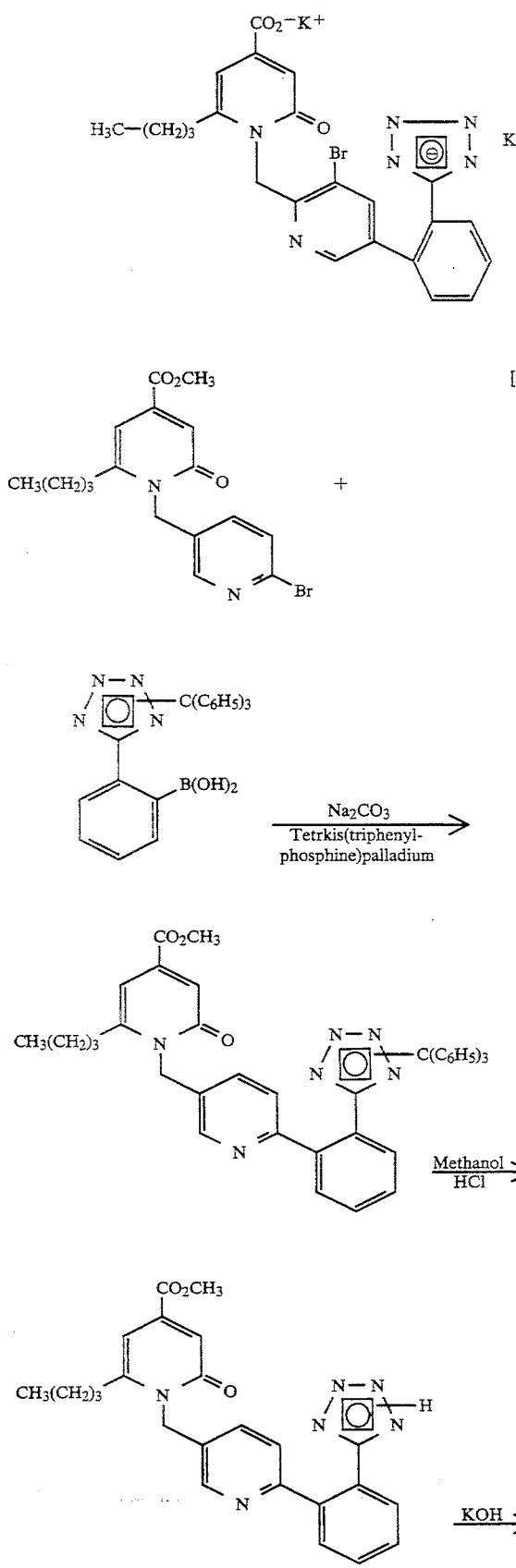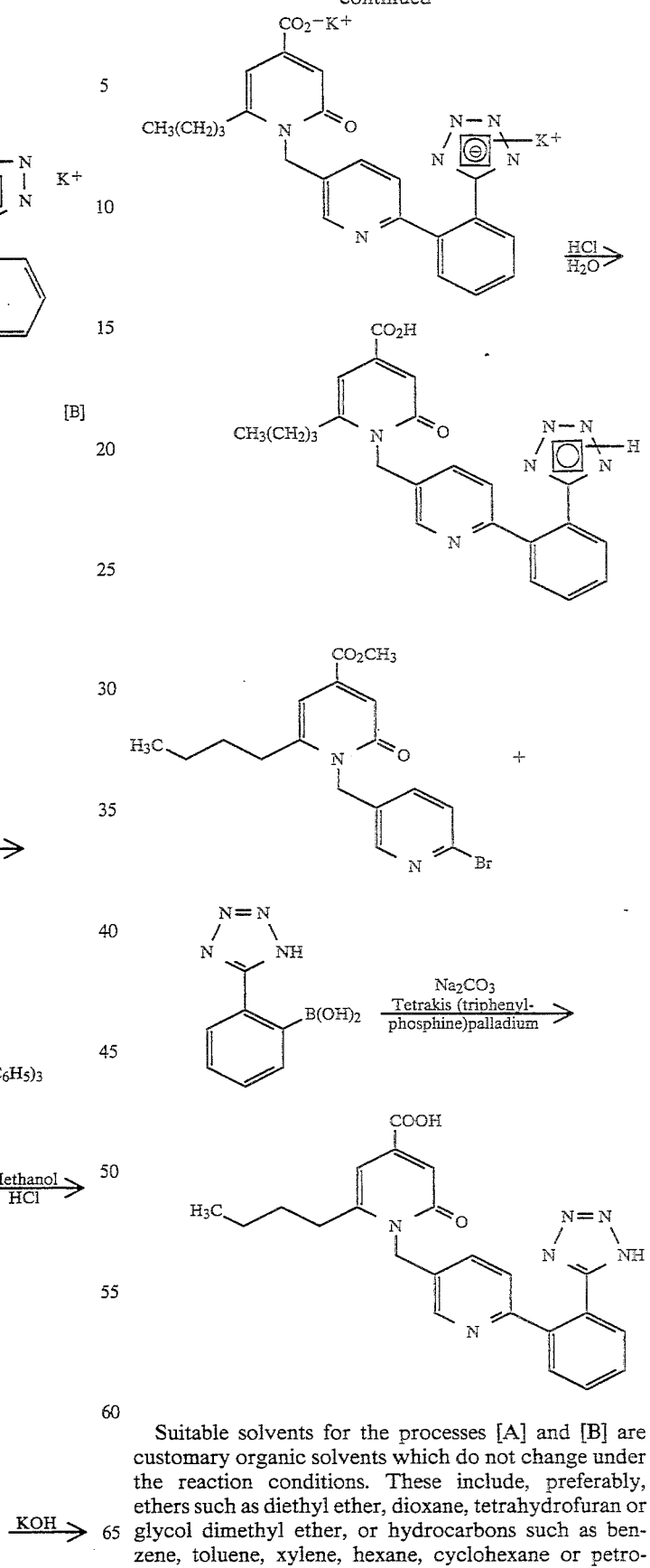

Suitable solvents for the processes [A] and [B] are customary organic solvents which do not change under the reaction conditions. These include, preferably, ethers such as diethyl ether, dioxane, tetrahydrofuran or glycol dimethyl ether, or hydrocarbons such as benzene, toluene, xylene, hexane, cyclohexane or petroleum fractions, or halogenohydrocarbons such as methylene chloride, trichloromethane, tetrachloromethane, dichloroethylene, trichloroethylene or chlorobenzene, or ethyl acetate, dimethyl sulphoxide, dimethylformamide or dimethoxyethane, hexamethylphosphoric acid triamide, acetonitrile, acetone or nitromethane. It is likewise possible to use mixtures of the solvents mentioned.

Tetrahydrofuran, acetone, dimethylformamide and dimethoxyethane are preferred for process [A]. Alcohols such as methanol, ethanol or propanol, and/or water are furthermore also suitable for process [B]. Toluene/methanol/water are preferred for process [B].

Bases which can be employed for the processes according to the invention are in general inorganic or organic bases. These include, preferably, alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate or caesium carbonate, or alkali metal or alkaline earth metal alcoholates or amides such as sodium methanolate or potassium methanolate, sodium ethanolate or potassium ethanolate or potassium tert-butylate, thallium carbonate or hydroxide, or lithium diisopropylamide (LDA), or organic amines (trialkyl($C_1$-$C_6$)amines, such as triethylamine, or heterocyclic compounds, such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals, such as sodium, or hydrides thereof such as sodium hydride, as bases. Potassium carbonate, sodium hydride, potassium tert-butylate or caesium carbonate are preferred for process [A]. Sodium carbonate is preferred for process [B].

The base is in general employed in an amount of 0.05 mol to 10 mol, preferably 1 mol to 2 mol, in each case per mole of the compounds of the formula (III) or (V).

The processes according to the invention are in general carried out in a temperature range from $-100°$ C. to $+100°$ C., preferably from 0° C. to 80° C. Process [B] according to the invention is in general carried out under an inert gas atmosphere.

The process according to the invention is in general carried out under normal pressure. However, it is also possible to carry out the process under increased pressure or under reduced pressure (for example in a range from 0.5 to 5 bar).

The triphenylmethyl group is eliminated with acetic acid or trifluoroacetic acid and water or one of the abovementioned alcohols or with aqueous hydrochloric acid in the presence of acetone or likewise with alcohols.

The elimination is in general carried out in a temperature range from 0° C. to 150° C., preferably from 20° C. to 100° C., under normal pressure.

Suitable catalysts for process [A] are potassium iodide or sodium iodide, preferably sodium iodide.

Suitable catalysts for process [B] are in general metal complexes of nickel, palladium or platinum, preferably palladium(0) complexes, such as, for example, tetrakistriphenylphosphinepalladium. It is likewise possible to employ phase transfer catalysts, such as, for example, tetra-n-butylammonium bromide or crown ethers.

The catalyst is employed in an amount of 0.0001 mol to 0.15 tool, preferably of 0.01 tool to 0.05 tool, per mole of the compound of the general formula (V).

The alkylation is in general carried out with alkylating agents such as, for example, ($C_1$-$C_8$)-alkyl halides, sulphonic acid esters or substituted or unsubstituted ($C_1$-$C_8$)-dialkyl- or ($C_1$-$C_8$)-diarylsulphonates, preferably methyl iodide or dimethyl sulphate.

The alkylation is in general carried out in one of the abovementioned solvents, preferably in dimethylformamide, in a temperature range from 0° C. to $+70°$ C., preferably from 0° C. to $+30°$ C., under normal pressure.

Suitable bases for the hydrolysis are the customary inorganic bases. These include, preferably, alkali metal hydroxides or alkaline earth metal hydroxides such as, for example, sodium hydroxide, potassium hydroxide or barium hydroxide, or alkali metal carbonates, such as sodium carbonate or potassium carbonate or sodium bicarbonate, or alkali metal alcoholates such as sodium methanolate, sodium ethanolate, potassium methanolate, potassium ethanolate or potassium tert-butanolate. Sodium hydroxide or potassium hydroxide are particularly preferably employed.

Suitable solvents for the hydrolysis are water or the customary organic solvents for hydrolysis. These include, preferably, alcohols such as methanol, ethanol, propanol, isopropanol or butanol, or esters such as tetrahydrofuran or dioxane, or dimethylformamide or dimethyl sulphoxide. Alcohols such as methanol, ethanol, propanol or isopropanol are particularly preferably used. It is likewise possible to employ mixtures of the solvents mentioned.

If appropriate, the hydrolysis can also be carried out with acids such as, for example, trifluoroacetic acid, acetic acid, hydrochloric acid, hydrobromic acid, methanesulphonic acid, sulphuric acid or perchloric acid, preferably with trifluoroacetic acid.

The hydrolysis is in general carried out in a temperature range from 0° C. to $+100°$ C., preferably from $+20°$ C. to $+80°$ C.

The hydrolysis is in general carried out under normal pressure. However, it is also possible to carry out the hydrolysis under reduced pressure or under increased pressure (for example from 0.5 to 5 bar).

In carrying out the hydrolysis, the base is in general employed in an amount of 1 to 3 mol, preferably of 1 to 1.5 mol, per mole of the ester. Molar amounts of the reactants are particularly preferably used.

The hydrolysis of tert-butyl esters is in general carried out with acids, such as, for example, hydrochloric acid or trifluoroacetic acid, in the presence of one of the abovementioned solvents and/or water or mixtures thereof, preferably with dioxane or tetrahydrofuran.

The amidation and the sulphonamidation are in general carried out in one of the abovementioned solvents, preferably in tetrahydrofuran or methylene chloride.

If appropriate, the amidation and the sulphonamidation can proceed via the activated stage of the acid halides, which can be prepared from the corresponding acids by reaction with thionyl chloride, phosphorus trichloride, phosphorus pentachloride, phosphorus tribromide or oxalyl chloride.

The amidation and the sulphonamidation are in general carried out in a temperature range from $-20°$ C. to $+80°$ C., preferably from $-10°$ C. to $+30°$ C., under normal pressure.

Suitable bases for this are, in addition to the abovementioned bases, preferably triethylamine and/or dimethylaminopyridine, DBU or DABCO.

The base is employed in an amount of 0.5 mol to 10 mol, preferably 1 mol to 2 mol, per mole of the corresponding acid or ester.

Acid-binding agents which can be employed for the sulphonamidation are alkali metal or alkaline earth metal carbonates such as sodium carbonate or potassium carbonate, alkali metal or alkaline earth metal hydroxides such as, for example, sodium hydroxide or potassium hydroxide, or organic bases such as pyridine, triethylamine, N-methylpiperidine or bicyclic amidines such as 1,5-diazabicyclo [3.4.0]-non-5-ene (DBN) or 1,5-diazabicyclo [3.4.0]undec-5-ene (DBU). Potassium carbonate is preferred.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride, or carbonyl compounds such as carbonyldiimidazole, or 1,2-oxazolium compounds such as 2-ethyl-5-phenyl-1,2-oxazolium 3-sulphonate, or propanephosphoric anhydride or isobutyl chloroformate or benzotriazolyloxy-tris-(dimethylamino)phosphoniumhexafluorophosphate or phosphonic acid diphenyl ester-aide or methanesulphonyl chloride, if appropriate in the presence of bases such as triethylamine or N-ethylmorpholine or N-methylpiperidine or dicyclohexylcarbodiimide and N-hydroxysuccinimide.

The acid-binding agents and dehydrating reagents are in general employed in an amount of 0.5 to 3 mol, preferably of 1 to 1.5 mol, per mole of the corresponding carboxylic acids.

The compounds of the general formula (II) are known in some cases or are new, and in this case can be prepared analogously to known methods.

The compounds of the general formula (III) are known per se.

The compounds of the general formula (IV) are new in most cases and can be prepared, for example, by a process in which compounds of the general formula (II) are reacted with compounds of the general formula (VI)

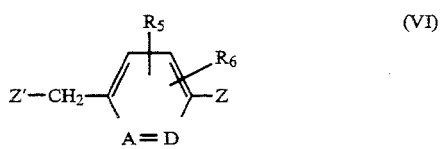

in which

A, D, $R^5$ and $R^6$ have the abovementioned meaning and

Z and Z' are identical or different and have the abovementioned meaning of Z, in one of the abovementioned solvents and in the presence of one of the bases described there, preferably in dimethoxyethane and caesium carbonate, at room temperature.

The bases are in general employed in an amount of 1 mol to 5 mol, preferably of 2 mol to 3 mol, per mole of the compounds of the general formula (VI).

The compounds of the general formula (VI) are known in most cases.

The compounds of the general formula (IV) are in general prepared in a temperature range from $-100°$ C. to $+100°$ C., preferably from $-20°$ C. to $+30°$ C., under normal pressure.

The compounds of the general formula (V) are new in the case where X=H and can be prepared, for example, by first reacting phenyltetrazole in an aprotic solvent and in the presence of a base under an inert gas atmosphere and then adding trimethyl borate, and, in a last step, hydrolysing the product with acids.

Suitable solvents for the process are aprotic solvents such as ethers, for example tetrahydrofuran, diethyl ether, toluene, hexane or benzene. Tetrahydrofuran is preferred.

Suitable bases are prim-, sec- and tert-butyllithium and phenyllithium. n-Butyllithium is preferred.

The base is employed in an amount of 2 mol to 5 mol, preferably of 2 mol to 3 mol, per mole of phenyltetrazole.

Suitable acids are in general mineral acids, such as, for example, hydrochloric acid, or $C_1$-$C_4$-carboxylic acids, such as, for example, acetic acid, or phosphoric acids. Hydrochloric acid is preferred.

The acid is in general employed in an amount of 1 mol to 10 mol, preferably of 1 mol to 3 mol.

The process is in general carried out in a temperature range from $-70°$ C. to $+25°$ C., preferably from $-10°$ C. to $0°$ C.

The process according to the invention is in general carried out under normal pressure. However, it is also possible to carry out the process under increased pressure or under reduced pressure (for example in a range from 0.5 to 5 bar).

The compounds of the general formula (Va) are known in some cases or can be prepared by customary methods.

The above preparation processes are mentioned merely for illustration. The preparation of the compounds of the general formula (I) according to the invention is not limited to these processes, and any modification of these processes can be used in the same manner for the preparation.

The substituted mono- and biphenyl methylpyridones according to the invention display an unforeseeable, valuable pharmacological action spectrum.

The compounds according to the invention have a specific A II-antagonistic action, since they competitively inhibit bonding of angiotensin II to the receptors. They suppress the vasoconstrictory and aldosterone secretion-stimulating effects of angiotensin II. They furthermore inhibit the proliferation of smooth muscle cells.

They can therefore be employed in medicaments for the treatment of arterial hypertension and atherosclerosis. They can moreover be employed for the treatment of coronary heart diseases, cardiac insufficiency, disturbances in cerebral performance, ischaemic cerebral diseases, disturbances in peripheral circulation, dysfunctions of the kidney and adrenal gland bronchospastic and vascular-related diseases of the respiratory passages, sodium retention and oedemas.

The compounds can also be used for the control of glaucoma, diabetic retinopathy and increases in the mobility of the intraocular retinal fluid.

They are also suitable for controlling diseases of the central nervous system such as for example depression, migraine, schizophrenia or anxiety states, brain dysfunctions, strokes, diabetic nephropathy, cardiac dysrhythmias, or for the prophylaxis of coronary heart diseases or restenosis after angioplasty and vascular surgery.

Investigation of the inhibition of contraction induced with agonists

Rabbits of both sexes are stunned by a blow to the neck and exsanguinated, or alternatively anaesthetized with Nembutal (about 60–80 mg/kg i.v.) and sacrificed by opening the thorax. The thoracic aorta is removed, freed from adhering connective tissue and divided into annular segments 1.5 nun wide, which are introduced individually, under an initial load of about 3.5 g, into 10 ml organ baths containing carbogen-gassed Krebs-Henseleit nutrient solution, temperature-controlled at 37° C., of the following composition: 119 mmol/l of NaCl; 2.5 mmol/l of $CaCl_2 \times 2$ $H_2O$; 1.2 mmol/l of $KH_2PO_4$; 10 mmol/l of glucose; 4.8 mmol/l of KCl; 1.4 mmol/l of $MgSO_4 \times 7$ $H_2O$ and 25 mmol/l of $NaHCO_3$.

The contractions are recorded isometrically by Statham UC2 cells via a bridge amplifier (from Mülheim or DSM Aalen) and digitized and evaluated by means of an A/D converter (system 570, Keithley Munich). The agonist dose/effect curves (DEC) are plotted hourly. With each DEC, 3 or 4 individual concentrations are introduced into the baths at intervals of 4 minutes. The end of the DEC and subsequent washing-out cycles (16 times for in each case about 5 seconds/minute with the abovementioned nutrient solution) is followed by a 28-minute resting or incubation phase, within which the contractions as a rule reach the starting value again.

The height of the 3rd DEC in the normal case is used as a reference parameter for evaluation of the test substance to be investigated in subsequent passes, this being introduced into the baths during the subsequent DECs at the start of the incubation time in a dosage which increases each time. Each aortic ring is stimulated the whole day with always the same agonist.

Agonists and their standard concentrations—application volume per individual dose=100 µl):

| | | |
|---|---|---|
| KCl | 22.7; 32.7; 42.7; 52.7 | mmol/l |
| Noradrenaline | $3 \times 10^{-9}$; $3 \times 10^{-8}$; $3 \times 10^{-7}$; $3 \times 10^{-6}$ | g/ml |
| Serotonin | $10^{-8}$; $10^{-7}$; $10^{-6}$; $10^{-5}$ | g/ml |
| B-HT 920 | $10^{-7}$; $10^{-6}$; $10^{-5}$ | g/ml |
| Methoxamine | $10^{-7}$; $10^{-6}$; $10^{-5}$ | g/ml |
| Angiotensin II | $3 \times 10^{-9}$; $10^{-8}$; $3 \times 10^{-8}$; $10^{-7}$ | g/ml |

The effect in each case at the 3rd=submaximum agonist concentration is taken as a basis for the calculation of the $IC_{50}$ (concentration at which the substance to be investigated causes 50% inhibition).

The compounds according to the invention inhibit the angiotensin II-induced contraction of the isolated rabbit aorta as a function of the dose. The contraction induced by potassium depolarization or other agonists was not inhibited or was inhibited only weakly at high concentrations.

Blood pressure measurements on rats infused with angiotensin II

Male Wistar rats (Moellegaard, Copenhagen, Denmark) with a body weight of 300–350 g are anaesthetized with thiopental (100 mg/kg i.p.). After tracheotomy, a catheter for blood pressure measurement is inserted into the femoral artery and a catheter for angiotensin II infusion and a catheter for administration of the substance are inserted into the femoral veins. After administration of the ganglionic blocker pentolinium (5 mg/kg i.v.), the angiotensin II infusion (0.3 µg/kg/minute) is started. As soon as the blood pressure values have reached a stable plateau, the test substances are administered either intravenously, or orally as a suspension or solution in 0.5% Tylose.

Determination of the antihypertensive activity on conscious hypertensive rats

The oral antihypertensive activity of the compounds according to the invention was tested on conscious rats with surgically induced unilateral renal arteriostenosis. For this, the right renal artery was constricted with a silver clip of 0.18 nun internal diameter. With this form of hypertension, the plasma renin activity is increased in the first six weeks after the intervention. The arterial blood pressure of these animals was measured bloodlessly using a "tail cuff" at defined intervals of time after administration of the substance. The substances to be tested were administered intragastrally ("orally") by a stomach tube in various doses as a suspension in a Tylose suspension. The compounds according to the invention lower the arterial blood pressure of the hypertensive rats in a clinically relevant dosage.

The compounds according to the invention furthermore inhibit specific bonding of radioactive angiotensin II as a function of the concentration.

Interaction of the compounds according to the invention with the angiotensin II receptor on membrane fractions from the adrenal cortex (bovine)

Bovine adrenal cortices (AC) which are freshly removed and carefully freed from the capsular medulla are comminuted to a coarse membrane homogenate in sucrose solution (0.32 M) with the aid of an Ultra-Turrax (Janke & Kunkel, Staufen, Bavaria) and partly purified to membrane fractions in two centrifugation steps. The investigations on receptor binding are carried out on partly purified membrane fractions of bovine AC using radioactive angiotensin II in an assay volume of 0.25 ml which contains, specifically, the partly purified membranes (50–80 µg), $^3$H-angiotensin II (3–5 nM), test buffer solution (50 mM Tris, pH 7.2 5 mM $MgCl_2$ and the substances to be investigated. After an incubation time of 60 minutes at room temperature, the non-bound radioactivity of the samples is separated by means of a moistened glass fibre filter (Whatman GF/C) and the bound radioactivity is measured spectrophotometrically in a scintillation cocktail, after washing the protein with ice-cold buffer solution (50 mM Tris/HCl, pH 7.4, 5% PEG 6000). The raw data were analysed with computer programs to $K_i$ and $IC_{50}$ values ($K_i$: $IC_{50}$ values corrected for the radioactivity used; $IC_{50}$ values: concentration at which the substance to be investigated causes 50% inhibition of the specific binding of the radioligand).

Investigation of the inhibition of the proliferation of smooth muscle cells by the compounds according to the invention Smooth muscle cells which are obtained from the aortas of rats by the media-explantate technique are used to determine the antiproliferative action of the compounds [R. Ross, J. Cell. Biol. 50, 172, 1971]. The cells are sown in suitable culture dishes, as a rule 96-well plates, and cultured for 2–3 days in medium 199 with 7.5% of FCS and 7.5% of NCS, 2 mM L-glutamine and 15 mM HEPES, pH 7.4 in 5% of $CO_2$ at 37°

C. Thereafter, the cells are synchronized by serum withdrawal for 2-3 days and then stimulated to growth with serum or other factors. At the same time, test compounds are added. After 16-20 hours, 1 μCi of ³H-thymidine is added, and after a further 4 hours, the incorporation of this substance into the DNA of the cells which can be precipitated with TCA is determined. The active compound concentration which causes half the maximum inhibition of the thymidine incorporation caused by 10% of FCS on sequential dilution of the active compound is calculated for determination of the IC$_{50}$ values.

The new active compounds can be converted in a known manner in the customary formulations, such as tablets, coated tablets, pills, granules, aerosols, syrups, emulsions, suspensions and solutions, using inert, nontoxic, pharmaceutically suitable excipients or solvents. The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and- /or dispersing agents, and, for example, in the case where water is used as the diluent, organic solvents can be used as auxiliary solvents if appropriate.

Administration is effected in the customary manner, preferably orally or parenterally, in particular perlingually or intravenously.

In the case of parenteral use, solutions of the active compound can be employed, using suitable liquid excipient materials.

In general, it has proved advantageous in the case of intravenous administration to administer amounts of about 0.001 to 1 mg/kg, preferably about 0.01 to 0.5 mg/kg of body weight to achieve effective results, and in the case of oral administration, the dosage is about 0.01 to 20 mg/kg, preferably 0.1 to 10 mg/kg of body weight.

Nevertheless, it may be necessary to deviate from the amounts mentioned, and in particular as a function of the body weight and the nature of the administration route, or of the behaviour of the individual towards the medicament, the nature of its formulation and the time or interval at which administration takes place. Thus in some cases it may be sufficient to manage with less than the abovementioned minimum amount, while in other cases the upper limit mentioned must be exceeded. Where relatively large amounts are administered, it may be advisable to divide these into a plurality of individual doses over the course of the day.

Starting compounds

EXAMPLE I

2-Methyl-5- [(trifluoromethyl) sulphonyloxy]-pyridine

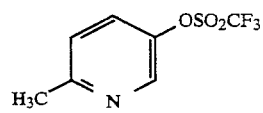

4.63 g (42.4 mmol) of 3-hydroxy-6-methylpyridine, 15.08 g (42.4 mmol) of N,N-bis-(trifluoromethanesulphonyl)aniline and 6.15 ml (44.53 mmol) of triethylamine are stirred overnight in 250 ml of methylene chloride. The reaction mixture is washed twice with 1 N sodium hydroxide solution, twice with aqueous potassium carbonate solution and twice with water and the organic phase is dried over sodium sulphate and concentrated on a rotary evaporator to give 10.47 g of an oil.

Yield: 100%

¹H-NMR (CDCl₃):δ=2.6 (3H, s); 7.2 (1H,m); 7.5 (1H,dd); 8.47 (1H, d)ppm.

Example II

2-Methyl-5-[2-triphenylmethyl-tetrazol-5-yl)phenyl]-pyridine

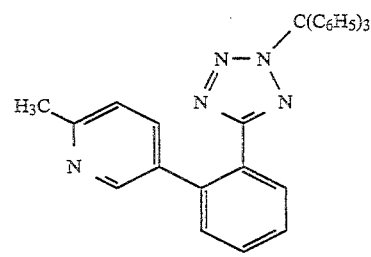

A suspension of 6.8 g (28.2 mmol) of the compound from Example 1, 20 g (46.3 mmol) of 3-(2'-triphenylmethyl-2'H-tetrazol-5'-yl)phenylboronic acid, 3 g (28.3 mmol) of sodium carbonate, 1.31 g (1.13 mmol of tetrakis (triphenylphosphine)palladium, 17.5 ml of water, 17.5 ml of methanol and 140 ml of toluene are stirred at 90° C. under an argon atmosphere for 4 hours. The reaction mixture is diluted with water and washed three times with ethyl acetate. The organic phase is washed with water and sodium chloride solution, dried over sodium sulphate, absorbed onto 150 g of silica gel and eluted on 200 g of silica gel with 1.6 l of ethyl acetate/- petroleum ether mixtures (1:10→1:1).

Yield: 9.15 g of a foam (67% of theory)

R$_f$=0.23 (ethyl acetate/petroleum ether 1:2, silica gel Si60)

EXAMPLE III

2-Bromomethyl-5-[2-(2-triphenylmethyl-tetrazol-5-yl)phenyl]pyridine

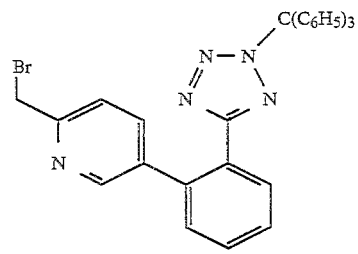

A suspension of 4.78 g (10 mmol) of the compound from Example II, 2 g (11.2 mmol) of N-bromosuccinimide and a spatula-tip of 2,2'-azo-bis-(2-methylpropionitrile) in 170 ml of carbon tetrachloride is heated under reflux overnight. The undissolved material is filtered off with suction, the solution is concentrated and the residue is chromatographed over silica gel using petroleum ether- /ethyl acetate 5:1 to give 1.2 g of the title compound.

Yield: 21.5% of theory $R_f$ (ethyl acetate/petroleum ether 1:5, silica gel)=0.34 0.8 g of

EXAMPLE IV

2-Bromomethyl-3-bromo-5-[2-(1-triphenylmethyl-tetrazol-5yl)phenyl]pyridine

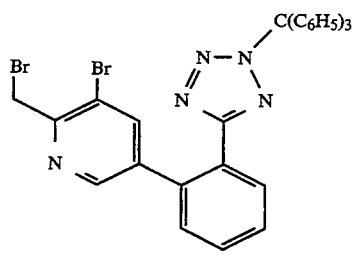

are furthermore eluted.

Yield: 14% of theory $R_f$ (ethyl acetate/petroleum ether 1:5, silica gel)=0.56

EXAMPLE V

6-Butyl-4-methoxycarbonyl-2-oxo-1-[(6-bromopyridin-3-ylmethyl]-1,2-dihydropyridine

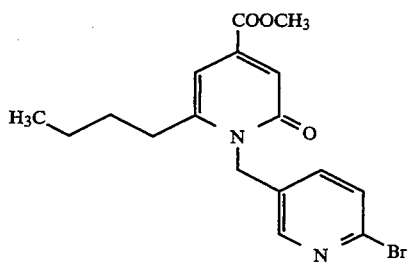

17.3 g of the title compound are obtained analogously to Example 1 from 30 g (0,143 mol) of 6-butyl-4-methoxycarbonyl-2-oxo-1,2-dihydropyridine, 45.5 g (0.17 mol of 2-bromo-5-bromomethylpyridine and 55.9 g (0.17 mol) of caesium carbonate in 0.6 l of dimethoxyethane.

Yield: 33.3% of theory $R_f$(ethyl acetate/petroleum ether 1:2)=0.14

EXAMPLE VI

6-Butyl-4-carboxy-2-oxo-1-[6-bromopyridin-3-ylmethyl]-1,2-dihydropyridine

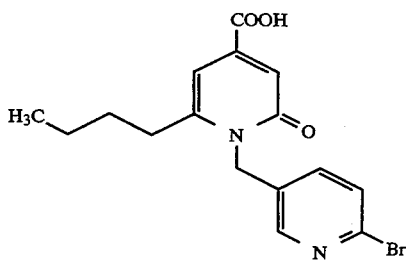

The title compound is obtained analogously to the instructions of Example 13 from the compound of Example V:

Yield: 100%

$R_f$(acetonitrile/water 5:1, silica gel)=0.47

EXAMPLE VII

4-Benzyloxycarbonyl-6-butyl-2-oxo-1-[6-bromopyridin-3-yl-methyl]-1,2-dihydropyridine

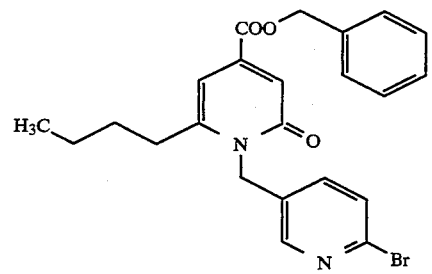

A suspension of 3.3 g (9 mmol) of the compound from Example VI, 0.1 g of dimethylaminopyridine, 4.7 ml (45 mmol) of benzyl alcohol and 2.05 g (9.9 mmol) of dicyclohexylcarbodiimide in 50 ml of methylene chloride is stirred overnight at 0° C. The precipitate which has separated out is filtered off with suction, the filtrate is concentrated and the resulting residue is chromatographed over 200 g of silica gel using ethyl acetate/petroleum ether mixtures 1:5-1:1 to give 3.4 g of the title compound.

Yield: 82.3% of theory $R_f$ (ethyl acetate/petroleum ether 1:2, silica gel)=0.25

EXAMPLE VIII

2 -(Tetrazol-5'-yl)phenylboronic acid

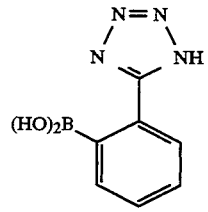

17.6 ml (44 mmol) of a 2.5 M solution of n-butyllithium in n-hexane are added to a solution of 2.9 g (20 mmol) of 5-phenyltetrazole in 50 ml of tetrahydrofuran at −5° C. under argon. The mixture is stirred at −5° C. to 0° C. for 30 minutes, and 10 ml (88 mmol) of trimethyl borate are added at this temperature. The cooling bath is then removed and 10 ml of half-concentrated hydrochloric acid are added to the solution at room temperature. After 1 hour, the mixture is extracted with 100 ml of ethyl acetate, the organic phase is separated off and the aqueous phase is extracted twice with 20 ml of ethyl acetate each time. The combined organic phases are dried over sodium sulphate and concentrated and the residue is purified over silica gel using toluene/glacial acetic acid/methanol (38:0.1:2).

Yield: 2.65 g (70% of theory)

$R_f$=0.26 (toluene/methanol/glacial acetic acid=32:8:1)

$^{13}$C-NMR:δ=156.7; 137.9; 133.5; 129.8; 128.9; 127.7; 126.9 ppm.

PREPARATION EXAMPLES

Example 1

6-Butyl-4-methoxycarbonyl-2-oxo-1-{5-[2-(triphenyl-methyltetrazol-5-yl)phenyl]pyridin-2-ylmethyl}-1,2-dihydropyridine

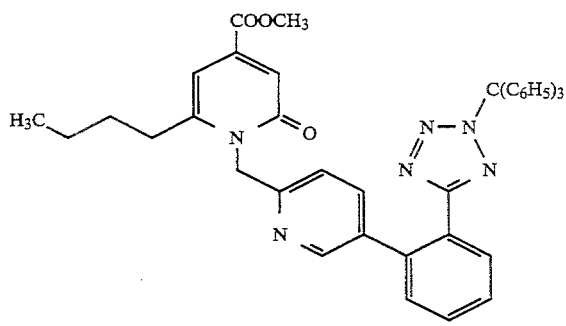

A suspension of 1.1 g (1.97 mmol) of the compound from Example III, 374 mg (1.79 mmol) of 6-butyl-4-methoxycarbonyl-2-oxo-1,2-dihydropyridine and 642 mg (1.97 mmol) of caesium carbonate are stirred in 15 ml of dimethoxyethane overnight. The reaction mixture is diluted with water and washed three times with ethyl acetate. The organic phase is washed with water and sodium chloride solution, dried with sodium sulphate and chromatographed over 70 g of silica gel using ethyl acetate/petroleum ether (1:2) to give 45 mg of an oil.

Yield: 3.3% of theory $R_f$ (silica gel, ethyl acetate/petroleum ether 1:1)=0.40

Example 2

Methyl 6-butyl-2-oxo-1-{6-[2-triphenylmethyl-(tetrazol-5-yl)-phenyl]-pyridin-3-ylmethyl)-1,2-dihydropyridine-4-carboxylate

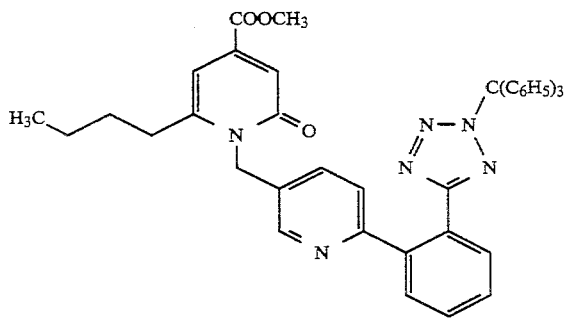

2.15 g of the title compound are obtained analogously to Example 1 from 1.98 g (5.55 mmol) of the compound from Example V and 2.59 g (6 mmol) of 3-(2'-triphenylmethyl2'-H-tetrazol-5'-yl)phenylboronic acid.

Yield: 56% of theory $R_f$(silica gel, ethyl acetate)=0.64

Example 3

Methyl 6-butyl-2-oxo-1-{5-[2-(1H-tetrazol-5-yl)phenyl]pyridin-2-ylmethyl)-1,2-dihydropyridine-4-carboxylate

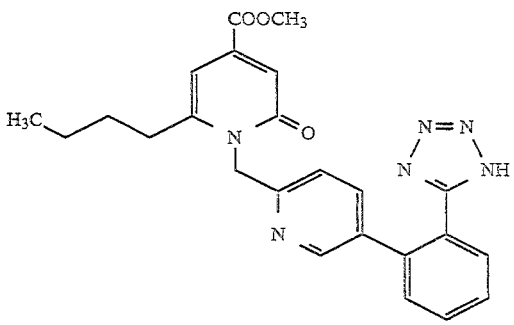

One drop of concentrated hydrochloric acid is added to 40 mg (0.06 mmol) of the compound from Example 1 in 2 ml of methanol and the mixture is stirred at room temperature for 2 hours. The reaction mixture is then chromatographed over 30 g of silica gel using ethylene chloride/methanol mixtures (10:1, 5:1, 0:1) to give 18.6 mg of the title compound.

Yield: 72.4% of theory

MS (FAB): 444 (M+), 445 (M++1)

Example 4

Dipotassium salt of 6-butyl-2-oxo-1-{5-[2-(1H-tetrazol-5-yl)-phenyl]-pyridin-2-ylmethyl}-1,2-dihydropyridine-4-carboxylic acid

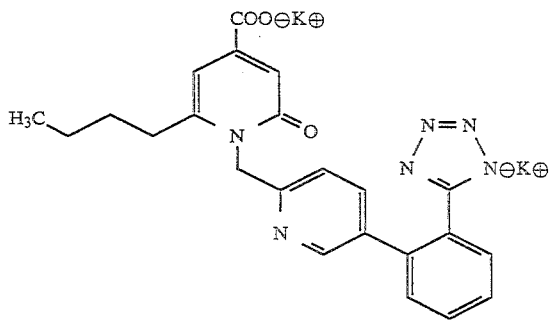

13.5 mg (0.03 mmol) of the compound from Example 3 are stirred in 2 ml of tetrahydrofuran and 0.6 ml of 0.1 N aqueous potassium hydroxide solution at 20° C. for 2 hours. The solvent is distilled off, the residue which remains is lyophilized and the product is dried in vacuo over phosphorus pentoxide to give 19.8 g of the title compound.

Yield: 100% of theory

MS (FAB): 429 (M+), 507 (M+1++2K)

The compounds listed in Table 1 are prepared analogously:

TABLE 1

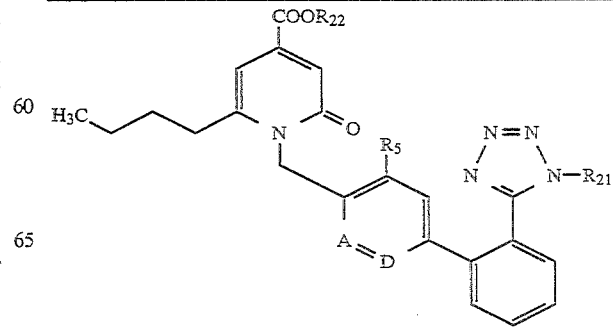

TABLE 1-continued

| Example No. | A | D | R22 | R21 | R5 | MS(FAB) | Starting Compound |
|---|---|---|---|---|---|---|---|
| 5 | N | CH | CH3 | H | Br | 523/525 (M+ + 1) | Example IV |
| 6 | N | CH | K | K | Br |  | Example 5 |
| 7 | CH | N | CH3 | H | H | 445 (M+ + 1) 467 (M+ + Na) | Example 2 |
| 8 | CH | N | K | K | H | 429 (M+ + 1) 507 (M+ + 1 + 2K) | Example 7 |

Example 9

6-Butyl-2-oxo-1-{6-[2-(1H-tetrazol-5-yl)phenyl]pyridin-3-ylmethyl}-1,2-dihydropyridine-4-carboxylic acid hydrochloride

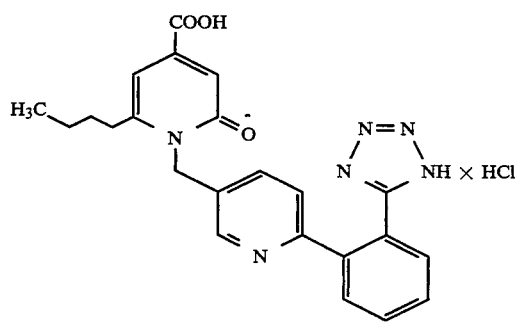

1.69 ml of 0.1 N hydrochloric acid are added to a solution of 28.5 mg (0.056 mmol) of the compound from Example 8 in 5 ml of water and the product is lyophilized to give 21.8 mg of the title compound.
Yield: 82.9% of theory
MS (FAB): 431

Example 10

Methyl 6-butyl-2-oxo-1-{6-[2-(1H-tetrazol-5-yl)phenyl]pyridin-3-ylmethyl)-1,2-dihydropyridine-4-carboxylate hydrochloride

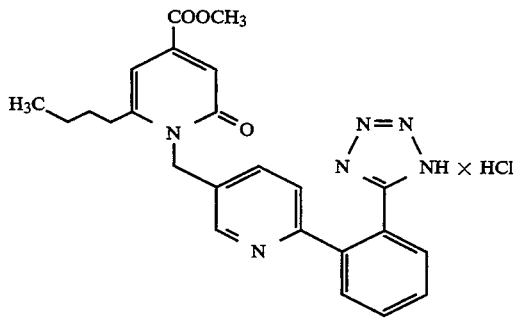

Hydrogen chloride gas is passed into a solution of 150 mg (0.34 mmol) of the compound from Example 7. The solvent is distilled off and the residue is dried over potassium hydroxide to give 144 mg of the title compound.
Yield: 88.7% of theory
MS (FAB): 445

Example 11

Potassium salt of methyl 6-butyl-2-oxo-1-{6-[2-(1H-tetrazol-5-yl)-phenyl]pyridin-3-ylmethyl}-1,2-dihydropyridine-4-carboxylate

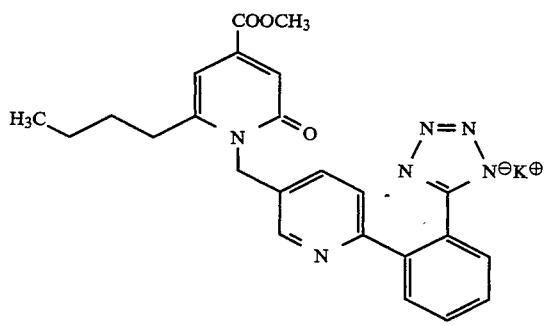

A solution of 16 mg (0.16 mmol) of potassium bicarbonate in 2 ml of water is added to a solution of 79.3 mg (0.16 mmol) of the compound from Example 7 in 6 ml of methanol/3 ml of tetrahydrofuran. The solvent is distilled off in vacuo at 20° C. and the residue is lyophilized to give 84.4 mg of the title compound.
Yield: 51.8% of theory
MS (FAB): 483

Example 12

Potassium salt of methyl 6-butyl-2-oxo-1-{5-[2-(1H-tetrazol-5-yl)-phenyl]pyridin-2-ylmethyl)-1,2-dihydropyridine-4-carboxylate

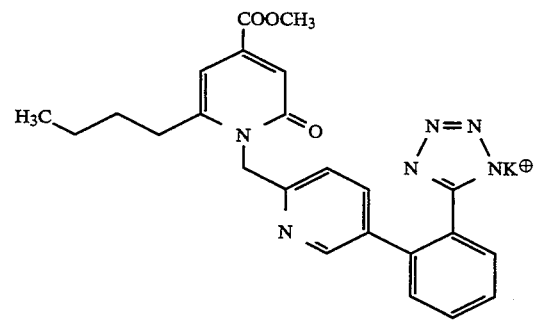

The title compound is obtained from the compound of Example 3 analogously to the instructions from Example 11.
Yield: 79% of theory
MS (FAB): 445(M+1) 467 (M+Na) 483 (M+K)

Example 13

6-Butyl-2-oxo-1-{5-[2-(1H-tetrazol-5-yl)-phenyl]pyridin-2-ylmethyl}-1,2-dihydropyridine-4-carboxylic acid.

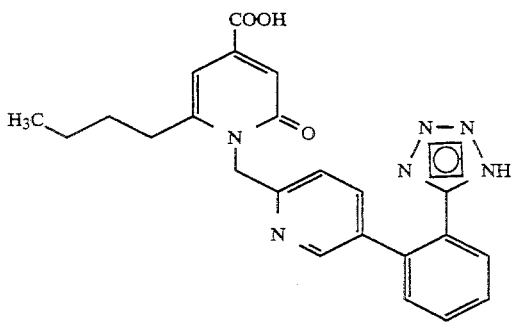

A solution of 5.9 mg (0.1 mmol) of the compound from Example 4 in 10 ml of water is brought to pH 2 with 1 N hydrochloric acid and washed three times with ethyl acetate. The combined organic phases are washed with water and saturated sodium chloride solution, dried over sodium sulphate and concentrated to give 38.3 mg of the title compound.

Yield: 76% of theory

MS (FAB): 431 (M+I)

Example 14

Benzyl 6-butyl-2-oxo-1-{6-[2-triphenylmethyl-(tetrazol-5-yl)-phenyl]pyridin-3-ylmethyl}-1,2-dihydropyridine-4-carboxybate

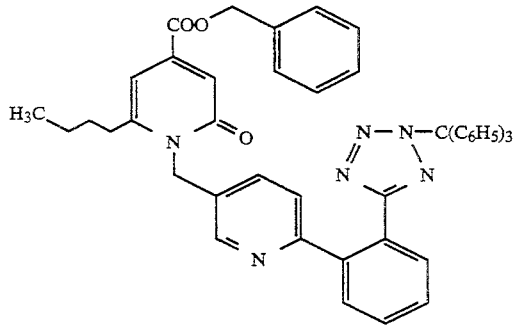

1.7 g of the title compound are obtained analogously to the instructions from Example 1 from 3.34 g (7.3 mmol) of the compound from Example VII and from 4.1 g (8 mmol) of 3-(2'-triphenylmethyl-2'-H-tetrazol-5'-yl)phenylboronic acid.

Yield: 31% of theory $R_f$ (ethyl acetate/petroleum ether 1:1, silica gel)=0.30

Example 15

Benzyl 6-butyl-2-oxo-1-{6-[2-(1H-tetrazol-5-yl)phenyl ]pyridin-3-ylmethyl}-1,2- dihydropyridine-4-carboxylate

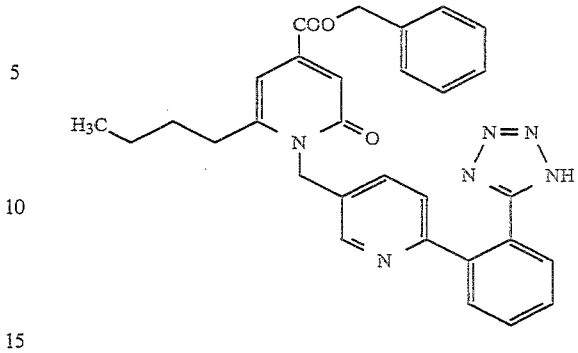

1.0 g of the title compound is obtained analogously to the instructions of Example 3 from 1.6 g (2 mmol) of the compound from Example 14.

Yield: 94% of theory

MS (FAB): 521 (M+H)

Example 16

Potassium salt of benzyl 6-butyl-2-oxo-1-{6-[2-(1H-tetrazol-5-yl)-phenyl]pyridin-3-ylmethyl}-1,2-dihydropyridin-4-carboxylate

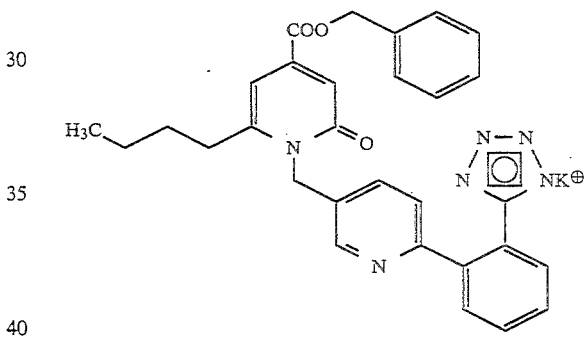

1.0 g of the title compound is obtained analogously to the instructions of Example 11 from 948 mg (1.8 mmol) of the compound from Example 15.

Yield: 98.3% of theory

MS (FAB): 521 (M+K), 559 (M+K)

We claim:

1. A substituted mono- or bipyridylmethylpyridone of the formula

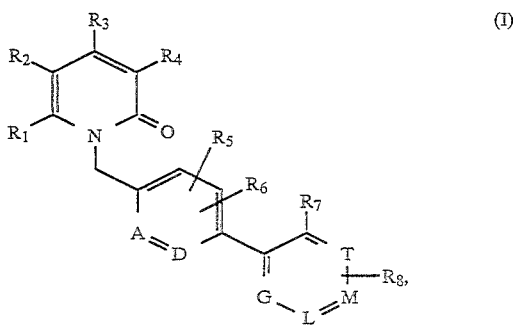

in which

A,D,G,L,M and T are identical or different and represent the CH group or represent a nitrogen atom, but wherein at least one of the radicals represents a nitrogen atom, but in each ring at most only one of the radicals represents a nitrogen atom, $R^1$ represents straight-chain or branched alkyl having up to 10 carbon atoms, which is optionally substituted by cycloalkyl having 3 to 6 carbon atoms, hydroxyl or by straight-chain or branched alkoxy or alkylthio having in each case up to 6 carbon atoms, or represents cycloalkyl having 3 to 6 carbon atoms, $R^2$, $R^3$ and $R^4$ are identical or different and represent hydrogen, hydroxyl, nitro, cyano, formyl or halogen, or represent straight-chain or branched alkyl, alkenyl, alkinyl, alkoxy or alkylthio having in each case up to 8 carbon atoms, which are optionally substituted up to 3 times in an identical or different manner by hydroxyl, cyano, halogen, carboxyl, straight-chain or branched alkoxy, acyl or alkoxycarbonyl having in each case up to 6 carbon atoms, or by cycloalkyl having 3 to 6 carbon atoms, benzyl, phenyl, phenoxy, benzoyl or by a 5- to 7-membered, saturated or unsaturated heterocyclic radical having up to 3 hetero atoms selected from the group consisting of S, N and O, wherein the cyclic radicals are optionally substituted up to 2 times in an identical or different manner by trifluoromethyl, trifluoromethoxy, halogen, nitro, cyano, hydroxyl, hydroxymethyl or by straight-chain or branched alkyl or alkoxy having in each case up to 6 carbon atoms, or represent straight-chain or branched acyl or alkoxycarbonyl having in each case up to 8 carbon atoms, phenoxycarbonyl, benzyloxycarbonyl or carboxyl, or represent tetrazolyl, which is optionally substituted by triphenylmethyl or by straight-chain or branched alkyl having up to 6 carbon atoms, which can in turn be substituted by cyano, halogen, carboxyl, phenoxycarbonyl, hydroxyl or by straight-chain or branched alkoxy or alkoxycarbonyl having in each case up to 6 carbon atoms, or represent a group of the formula

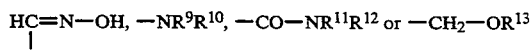

wherein
$R^9$, $R^{10}$, $R^{11}$ and $R^{12}$ are identical or different and denote hydrogen, cycloalkyl having 3 to 8 carbon atoms or straight-chain or branched alkyl having up to 8 carbon atoms, which is optionally substituted by phenyl, or
$R^9$ and $R^{10}$, together with the nitrogen atom, form a 5- to 6-membered, saturated heterocyclic radical having up to 2 further hetero atoms selected from the group consisting of S, N and O,
$R^{13}$ denotes straight-chain or branched acyl having up to 6 carbon atoms or benzoyl,
$R^5$, $R^6$ and $R^8$ are identical or different and represent hydrogen, halogen, cyano, nitro, hydroxyl, trifluoromethyl or amido or represent straight-chain or branched alkyl, alkoxy or alkoxycarbonyl having up to 6 carbon atoms,
$R^7$ represents a group of the formula $-CO-R^{14}$, $-SO_2R^{15}$, $-CO-NR^{16}R^{17}$, $-NH-SO_2R^{16}$, or denotes $-SO_2NR^{19}R^{20}$,
wherein
$R^{14}$ denotes hydroxyl or straight-chain or branched alkoxy having up to 6 carbon atoms,
$R^{15}$ denotes hydroxyl, trifluoromethyl, straight-chain or branched alkoxy or alkyl having in each case up to 6 carbon atoms, phenyl or benzyl, which can optionally be substituted up to 2 times in an identical or different manner by halogen, trifluoromethyl or straight-chain or branched alkyl having up to 4 carbon atoms,
$R^{16}$ and $R^{17}$ are identical or different and have the abovementioned meaning of $R^{11}$ and $R^{12}$, or
$R^{16}$ denotes hydrogen and
$R^{17}$ denotes the group $-SO_2R^{15}$, wherein
$R^{15}$ has the abovementioned meaning, has the abovementioned meaning of $R^{15}$ and is identical to or different from this,
$R^{19}$ and $R^{20}$ have the abovementioned meaning of $R^9$ and $R^{10}$ and are identical to or different from these, or
$R^{19}$ denotes hydrogen or straight-chain or branched alkyl having up to 4 carbon atoms and
$R^{20}$ has the abovementioned meaning of $R^{15}$ and is identical to or different from this, or
$R^7$ represents a radical of the formula

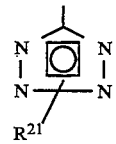

wherein
$R^{21}$ denotes hydrogen or straight-chain or branched alkyl having up to 8 carbon atoms, which is optionally substituted by straight-chain or branched acyl having up to 6 carbon atoms, or denotes the triphenylmethyl group,
or a salt thereof.

2. A substituted mono- or bipyridylmethylpyridone according to claim 1
wherein
A, D, G, L, M and T are identical or different and represent the CH group or represent a nitrogen atom, but wherein at least one of the radicals represents a nitrogen atom, but in each ring at most only one of the radicals represents a nitrogen atom,
$R^1$ represents straight-chain or branched alkyl having in each case up to 8 carbon atoms, which is optionally substituted by cyclopropyl, cyclopentyl, cyclohexyl, hydroxyl or by straight-chain or branched alkoxy or alkylthio having in each case up to 4 carbon atoms, or represents cyclopropyl, cyclopentyl or cyclohexyl,
$R^2$, $R^3$ and $R^4$ are identical or different and represent hydrogen, hydroxyl, nitro, cyano, formyl, fluorine, chlorine, bromine or iodine, or represent straight-chain or branched alkyl, alkenyl, alkinyl, alkoxy or alkylthio having in each case up to 6 carbon atoms, which are optionally substituted by hydroxyl, cyano, fluorine, chlorine, bromine, carboxyl, straight-chain or branched alkoxy, acyl or alkoxycarbonyl having in each case up to 4 carbon atoms, or by benzyl, phenyl, phenoxy, benzoyl or thienyl, wherein the cyclic radicals are optionally substituted by trifluoromethoxy, trifluoromethyl, hydroxymethyl, fluorine, chlorine, bromine, iodine or by straight-chain or branched alkyl or alkoxy having in each case up to 6 carbon atoms, or represent straight-chain or branched acyl or alkoxycarbonyl having in each case up to 6 carbon atoms, phenoxycarbonyl, benzyloxycarbonyl or carboxyl, or represent tetrazolyl, which is optionally substituted by triphenylmethyl or by straight-chain or branched alkyl having up to 5 carbon atoms, which can in turn be substituted by cyano, fluorine, chlorine, bromine, carboxyl, hydroxyl or by straight-chain or branched alkoxy or alkoxycarbonyl having in each case up to 4 carbon atoms, or represent a group of the formula

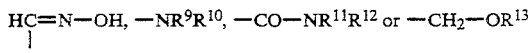

wherein
- $R^9$, $R^{10}$, $R^{11}$ and $R^{12}$ are identical or different and denote hydrogen, cyclopropyl, cyclopentyl, cyclohexyl or straight-chain or branched alkyl having up to 6 carbon atoms, which is optionally substituted by phenyl, or
- $R^9$ and $R^{10}$, together with the nitrogen atom, form a morpholine ring,
- $R^{13}$ denotes straight-chain or branched acyl having up to 6 carbon atoms or benzoyl,
- $R^5$, $R^6$ and $R^8$ are identical or different and represent hydrogen, fluorine, chlorine, bromine, trifluoromethyl or hydroxyl or represent straight-chain or branched alkyl or alkoxy having in each case up to 4 carbon atoms,
- $R^7$ represents a group of the formula $-CO-R^{14}$, $-SO_2R^{15}$, $-CO-NR^{16}R^{17}$, $-NH-SO_2R^{18}$ or $-SO_2-NR^{19}R^{20}$, wherein
- $R^{14}$ denotes hydroxyl or straight-chain or branched alkoxy having up to 4 carbon atoms,
- $R^{15}$ denotes straight-chain or branched alkyl having up to 4 carbon atoms, benzyl, trifluoromethyl or p-tolyl,
- $R^{16}$ and $R^{17}$ are identical or different and have the abovementioned meaning of $R^{11}$ and $R^{12}$ or
- $R^{16}$ denotes hydrogen and
- $R^{17}$ denotes the group $-SO_2R^{15}$, wherein $R^{15}$ has the abovementioned meaning,
- $R^{18}$ has the abovementioned meaning of $R^{15}$ and is identical to or different from this,
- $R^{19}$ and $R^{20}$ have the abovementioned meaning of $R^9$ and $R^{10}$ and are identical to or different from these, or
- $R^{19}$ denotes hydrogen or methyl,
- $R^{20}$ has the abovementioned meaning of $R^{15}$ and is identical to or different from this or
- $R^7$ represents a radical of the formula

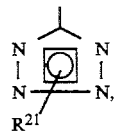

wherein
- $R^{21}$ denotes hydrogen or straight-chain or branched alkyl having up to 6 carbon atoms, which is optionally substituted by straight-chain or branched acyl having up to 4 carbon atoms, or denotes the triphenylmethyl group, or a salt thereof.

3. A substituted mono- or bipyridylmethylpyridone according to claim 1
wherein
- A,D,G,L,M and T are identical or different and represent the CH group or represent a nitrogen atom, but wherein at least one of the radicals represents a nitrogen atom, but in each ring at most only one of the radicals represents a nitrogen atom,
- $R^1$ represents straight-chain or branched alkyl having up to 6 carbon atoms, or represents cyclopropyl, cyclopentyl or cyclohexyl,
- $R^2$, $R^3$ and $R^4$ are identical or different and represent hydrogen, hydroxyl, cyano, formyl, fluorine, chlorine, bromine or iodine, or represent straight-chain or branched alkyl or alkoxy having in each case up to 4 carbon atoms, represent straight-chain or branched alkoxy carbonyl having up to 4 carbon atoms, phenoxycarbonyl, benzyloxycarbonyl or carboxyl, or
- $R^5$, $R^6$ and $R^8$ are identical or different and represent hydrogen, hydroxyl, fluorine, chlorine, bromine or methyl,
- $R^7$ represents a group of the formula $-CO-R^{14}$, wherein
- $R^{14}$ denotes hydroxyl or straight-chain or branched alkoxy having up to 4 carbon atoms, or
- $R^7$ represents the tetrazolyl radical of the formula

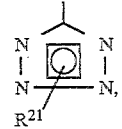

wherein
- $R^{21}$ denotes hydrogen or straight-chain or branched alkyl having up to 4 carbon atoms, which is optionally substituted by straight-chain or branched acyl having up to 4 carbon atoms, or phenoxycarbonyl, benzyloxycarbonyl or carboxyl, or
- $R^5$, $R^6$ and $R^8$ are identical or different and represent hydrogen, hydroxyl, fluorine, chlorine, bromine or methyl,
- $R^7$ represents a group of the formula $-CO-R^{14}$, wherein
- $R^{14}$ denotes hydroxyl or straight-chain or branched alkoxy having up to 4 carbon atoms, or
- $R^7$ represents the tetrazolyl radical of the formula

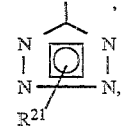

wherein
- $R^{21}$ denotes hydrogen or straight-chain or branched alkyl having up to 4 carbon atoms, which is optionally substituted by straight-chain or branched acyl having up to 4 carbon atoms, or denotes the triphenylmethyl group, or a thereof.

4. A substituted mono- or bipyridylmethylpyridone according to claim 1 wherein
- A or D represents a nitrogen atom and the other substituents represent the CH group, R¹ represents straight-chain or branched alkyl having up to 4 carbon atoms, R², R³ and R⁴ are identical or different and represent hydrogen, carboxyl or represent straight-chain or branched alkoxycarbonyl having up to 4 carbon atoms, R⁵, R⁶ and R⁸ are identical or different and represent hydrogen, fluorine, chlorine, bromine or methyl, R⁷ represents a group of the formula —CO—R⁴, wherein R¹⁴ denotes hydroxyl or straight-chain or branched alkoxy having up to 4 carbon atoms or R⁷ represents the tetrazolyl radical of the formula

wherein

R²¹ denotes hydrogen or the triphenylmethyl group, or a salt thereof.

5. A substituted monopyridylmethylpyridone compound according to claim 1 wherein such compound is Methyl 6-butyl-2-oxo-1-(5-[2-(1H-tetrazol-5-yl)-phenyl]pyridin-2-ylmethyl}-1,2-dihydropyridine-4-carboxylate of the formula

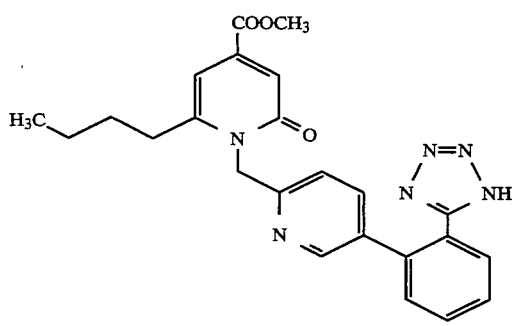

or a salt thereof.

6. A substituted monopyridylmethylpyridone compound according to claim 1 wherein such compound is 6-Butyl-2-oxo-1-(6-[2-(1H-tetrazol-5-yl)phenyl]pyridin-3-ylmethyl}-1,2-dihydropyridine-4-carboxylic acid of the formula

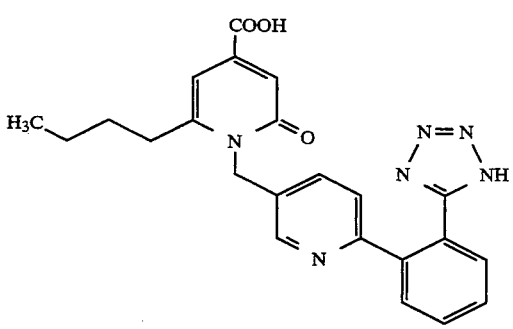

or a salt thereof.

7. A substituted moropyridylmethylpyridone compound according to claim 1 wherein such compound is Methyl 6-butyl-2-oxo-1-{6-[2-(1H-tetrazol-5-yl)-phenyl]pyridin-3-ylmethyl}-1,2-dihydropyridine-4-carboxylate of the formula

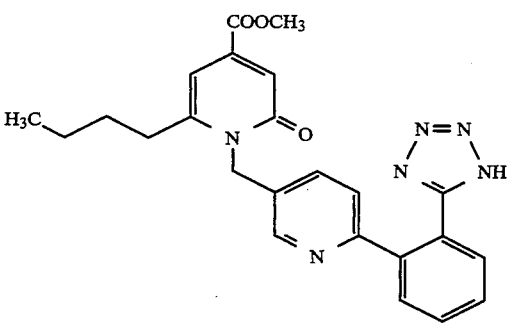

or a salt thereof.

8. A monopyridylmethylpyridone compound monopyridylmethylpyridone compound according to claim 1 wherein such compound is Butyl-2-oxo-1-(5-[2-(1H-tetrazol-5-yl)-phenyl]pyridin-2-ylmethyl)-1,2-dihydroproyridine-4 carboxylic acid of the formula

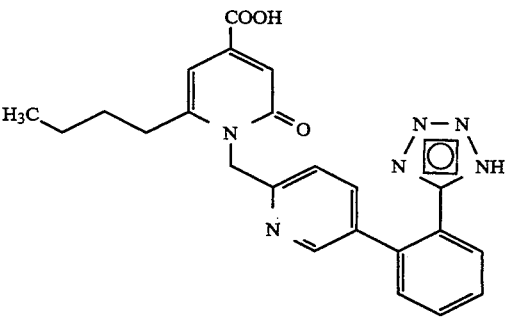

or a salt thereof.

9. A composition for the treatment of arterial hypertension and atherosclerosis comprising an amount effective therefore of a compound or salt thereof according to claim 1 and a pharmacologically acceptable diluent.

10. A method of treating arterial hypertension and atherosclerosis in a patient in need thereof which comprises administering to such patient an amount effective therefore of a compound or salt thereof according to claim 1.

* * * * *

UNITED STATES PATENT AND TRADEMARK OFFICE
CERTIFICATE OF CORRECTION

PATENT NO. : 5,407,948    Page 1 of 2
DATED : April 18, 1995
INVENTOR(S) : Fey, et al.

It is certified that error appears in the above-indentified patent and that said Letters Patent is hereby corrected as shown below:

| | |
|---|---|
| Col. 27, line 62 | Delete " $-NH-SO_2R^{16}$ " and substitute -- $-NH-SO_2R^{18}$ -- |
| Col. 28, line 10 | After " meaning, " insert -- $R^{18}$ -- |
| Col. 31, line 11 | Delete " $-CO-R^4$ " and substitute -- $CO-R^{14}$ -- |
| Col. 31, line 28 | Delete second formula " 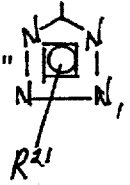 " |
| Col. 31, claim 5 line 3 | After " oxo-1- " delete " ( " and substitute --{-- |
| Col. 31, claim 6 line 3 | After " oxo-1 " delete " ( " and substitute --{-- |

UNITED STATES PATENT AND TRADEMARK OFFICE
CERTIFICATE OF CORRECTION

PATENT NO. : 5,407,948
DATED : April 18, 1995
INVENTOR(S) : Fey, et al.

It is certified that error appears in the above-indentified patent and that said Letters Patent is hereby corrected as shown below:

Col. 32, line 37    After " oxo-1- " delete " ( " and substitute --{ --

Signed and Sealed this

Eighteenth Day of July, 1995

Attest:

BRUCE LEHMAN

Attesting Officer    Commissioner of Patents and Trademarks